United States Patent [19]

Albrektsson et al.

[11] Patent Number: 4,880,006
[45] Date of Patent: Nov. 14, 1989

[54] BONE INGROWTH CHAMBER

[75] Inventors: Tomas Albrektsson, Mölndal; Per Aspenberg, Lund, both of Sweden

[73] Assignee: Nobelpharma AB, Gothenburg, Sweden

[21] Appl. No.: 124,149

[22] Filed: Nov. 23, 1987

[30] Foreign Application Priority Data

Nov. 21, 1986 [SE] Sweden ................................ 8604973

[51] Int. Cl.⁴ .............................................. A61B 5/00
[52] U.S. Cl. .................................... 128/630; 623/66; 623/16
[58] Field of Search ..................... 128/630; 623/16, 66; 73/508

[56] References Cited

U.S. PATENT DOCUMENTS 4,055,799 10/1977 Coster et al. ................... 128/630 X
4,066,068  1/1978 Nilsson et al. ................. 128/630 X
4,330,891  5/1982 Branemark ............................ 623/16
4,732,155  3/1988 Zetter et al. ......................... 118/630

OTHER PUBLICATIONS

BIOMATERIALS AND BIOMECHANICS, 1983, pp. 238–288, Elsevier Science Publishers B. V., Amsterdam, N.L.T.; Albrektsson et al.; "The Harvest Chamber—A Newly Developed Implant for Analysis of Bone Remodelling in Situ".
ACTA RADIOLAGICA ONCOLOGY, vol. 25, No. 1, 1986, pp. 27–62, Gothenburg, SE.; M. Jacobsson et al.: "Provoked Repetitive Healing of Mature Bone Tissue Following Irradiation".
ACTA ONCOLOGICA, vol. 26, No. 1, 1987, pp. 63–63, Gothenburg, SE.; P. Kalebo et al.: "Bone Healing Following Irradiation During Tourniquet Ischaemia".
P-I Branemark et al., "Osseointegrated Titanium Fixtures in the Treatment of Edentulousness"-Biomaterials, 1983, vol. 4, Jan.
Richard Skalak, "Biomechanical Considerations in Osseointegrated Prostheses", The Journal of Prosthetic Dentistry, Jun. 1983, vol. 49, No. 6.

Primary Examiner—Max Hindenburg
Assistant Examiner—John P. Lacyk
Attorney, Agent, or Firm—Pollock, Vande Sande & Priddy

[57] ABSTRACT

An apparatus for studying the bone formation or bone ingrowth in an implant, in response to locally administered test substances of different types, is made of biocompatible material, preferably pure titanium, and is implanted in living bone tissue, primarily for animal experiment activities. The apparatus has an outer portion with a central recess in which an inner portion is removably inserted. The two portions form, in the assembled state, a bone tissue ingrowth channel which is exposed when the inner portion is removed, whereby allowing examination of tissue which has grown into the channel. The inner portion includes a reservoir for the test substance whose bone formation promoting properties are to be tested. The reservoir is connected to the bone tissue ingrowth channel through a capillary aperture, so-called diffusion capillary, for supply of the test substance without simultaneous liquid flow.

12 Claims, 2 Drawing Sheets

BONE INGROWTH CHAMBER

TECHNICAL FIELD

The present invention relates to an apparatus for studying bone ingrowth in an implant in response to a locally administered test substance. The apparatus is primarily intended for use in animal experimental activities, but a certain clinical, experimental use may also occur. The apparatus is of a biocompatible material, preferably titanium, and is intended to be implanted in living bone tissue.

BACKGROUND ART

It is previously known in this art how artificial implants may be anchored directly in bone tissue. In order to avoid the risk of loosening or detachment, every attempt is made to achieve a direct contact, that is an exact adaptation between the implant and the surrounding bone tissue, so-called osseointegration. Such an exact adaptation may be achieved by sophisticated operational technique and by a suitable design of the implant. The osseointegration principle developed by professor Brånemark et al has successfully been used clinically for 20 years for maxillary-anchored dental bridges and is described in, for example:

P-I Brånemark et al, "Osseointegrated titanium fixtures in the treatment of edentulousness". Biomaterials, 1983. Vol 4, January; and Rickard Skalak, "Biomechanical considerations in osseointegrated prostheses". The Journal of Prosthetic Dentistry, June 1983, Volume 49, Number 6.

The principle is based on the fact that the implant is of pure titanium, at least in the interface zone between living tissue and implant. Swedish patent specification No. 79.02035-0 corresponding to U.S. Pat. No. 4,330,891 also discloses and describes the importance of the surface structure of the titanium for a powerful connection between the living bone tissue and the implant. By a special so-called microporous surface structure of the implant, the preconditions are further improved for a more or less permanent anchorage of the implant in the tissue.

To be able to assess the preconditions and potential for different implants to form a permanent anchorage with the tissue, there is a need to be able to study in greater detail and under standardized conditions the bone ingrowth of the implant and also those phases which precede the bone formation itself. Thus, it is previously known in this art how a special examination chamber may be operated into the bone tissue of a living animal, the chamber being designed such that samples of newly-formed bone tissue may be harvested from the chamber at regular intervals, and be examined. Hence, the chamber makes possible a quantification of bone ingrowth/implant incorporation under different experimental conditions without the need of sacrificing the animal. Such a test chamber, "The Harvest Chamber", is described in T. Albrektsson, M. Jacobsson and P. Kälebo, "The Harvest Chamber—A newly developed Implant for Analysis of Bone Remodelling in situ", Biomaterials and Biomechanics 1983, pp. 283-288.

From such disclosures as the above-mentioned Swedish patent specification No. 79.02035-0, it is apparent that certain substances possess bone growth promoting properties, for example they increase or hasten the growth of bone tissue into an implant and, by such means, shorten the healing time required for the implant. However, prior art methods for studying the effects of such various substances on bone growth have not been without their problems. First, it is difficult to administer a potentially bone-stimulating substance locally and, moreover, it is no easy matter to establish that such a substance actually reaches the tissue which is to be examined. Secondly, the evaluation of the new tissue formed once the substance has been added requires with all certainty that the newly-formed bone tissue can be distinguished from existing bone tissue. A number of solutions to these problems have been proposed earlier. For example, biomechanical tests have been employed to examine the effects of prostaglandin on animal bone tissue. Furthermore, scintigraphic methods have been employed to investigate hormonal growth promoting properties on demineralized cortical bone. Methods based on tetracycline treatment are also previously known in the art.

OBJECT OF THE PRESENT INVENTION

The object of the present invention is to provide an apparatus for testing the potentially bone-stimulating/retarding effect of a locally administered substance and which obviates the above-indicated problems. To this end, the present invention is based on a test chamber/implant as described above but which has been modified such that local administration of a test substance in liquid form is permitted. The present invention includes an outer portion with a central recess and a removable inner portion inserted in the recess, these together forming a bond growth through channel which is intended to be exposed, when the inner portion is removed, in order to make possible examination of tissue which has grown into the channel. The inner portion further comprises a reservoir connected to the bone growth channel for the administration of the test substance under consideration herein.

In one preferred embodiment of the present invention, the reservoir is in communication with the bone growth channel by the intermediary of a capillary opening, so-called diffusion capillary, for the administration of the test substance in question without simultaneous liquid flow.

BRIEF DESCRIPTION OF THE ACCOMPANYING DRAWINGS

The nature of the present invention and its aspects will be more readily understood from the following brief description of the accompanying Drawings, and discussion relating thereto.

In the accompanying Drawings.

DETAILED DESCRIPTION OF PREFERRED EMBODIMENT

As was mentioned by way of introduction, the apparatus, hereinafter designated the implant, is based on the previously known so-called "harvest chamber" which consists of a cylindrical outer portion of pure titanium and an inner, removable central portion. Two diametrically opposed holes are provided in the outer portion which cooperate with grooved recesses in both portions such that an open through channel is formed when the implant is assembled. Once the implant has been inserted in a known manner in the bone tissue, for example in the tibia of a rabbit, a bone formation process commences and the channel is duly filled with newly-formed bone tissue. The bone formation process and the ingrown bone tissue may be studied at regular intervals by removing the central portion of the implant.

Figure 1:
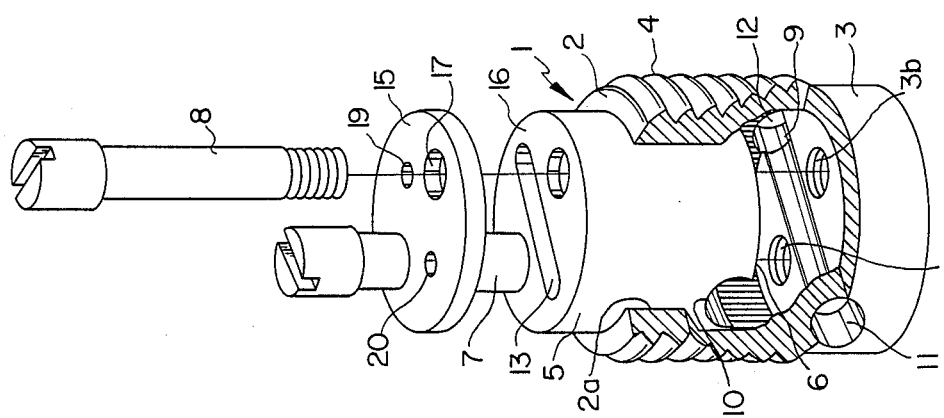
FIG. 1 is an exploded view of the entire apparatus partly in section.

FIG. 1 shows an implant 1 according to the present invention which, as opposed to the prior art apparatus (the Harvest Chamber) permits the local administration of a test substance. The implant is of pure titanium and comprises an outer, cylindrical portion 2, with a central recess 2a and a base plate 3. The cylindrical portion is provided with an outer thread 4 for the careful threading of the implant into a bore in the bone tissue. Advantageously, use is made of the atraumatic insertion technique of titanium implants as is previously known from Professor Branemark's maxillary-anchored dental bridges, this constituting a precondition for osseointegration. The outer, cylindrical portion 2 is open at its top and permits an inner, cylindrical portion 5 to be inserted such that this portion rests with its lower end surface 6 against the base plate 3. The inner, central portion 5 is fixedly locked to the outer portion 2 by means of two locking screws 7, 8 which are screwed in place in two threaded holes 3a, 3b in the base plate. On its inner surface, the base plate 3 is provided with a recessed groove 9 which cooperates with a corresponding recesed groove 10 in the lower end surface 6 of the central portion. Two holes 11, 12 diametrically disposed in the circumferential surface of the outer portion also cooperate with the grooved recesses such that a through channel is formed for bone ingrowth. Instead of forming the bone growth channel by two cooperating recessed grooves 9, 10 in the base plate and the central portion, respectively, the channel may also be formed by a grooved recess in the central portion, while the interior defining surface of the base plate is planar. In such instance, the grooved recess in the central portion is made slightly deeper.

Figure 2:
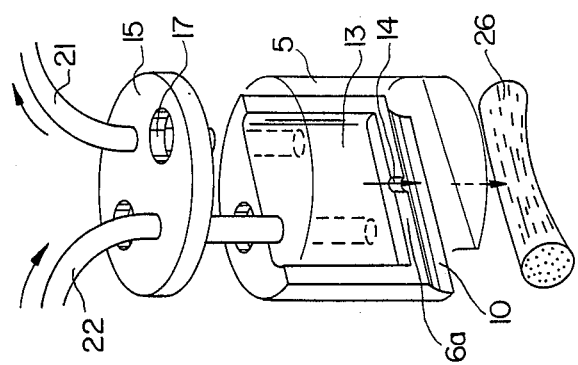
FIG. 2 illustrates the central portion of the apparatus with a reservoir for the administered solution whose bone growth promoting properties are to be tested.

The central portion 5 further includes a liquid reservoir 13 which is in communication with the bone growth channel through a narrow capillary aperture 14, a so-called diffusion capillary, in the bottom of the reservoir (see FIG. 2). Hereby, administration, or supply, of test substance will be effected without, at the same time, causing liquid flow to the channel. At its top, the liquid reservoir is covered by a cover plate 15 which is locked against the upper end surface 16 of the central portion by the locking screws 7 and 8. Apart from two holes 17 and 18 for the locking screws, the cover plate 15 is also provided with two holes 19 and 20 above the liquid reservoir for hoses 21, 22 for the supply and removal, respectively, of liquid/testing substance. A sealing washer of silicon rubber or the like (not shown) may advantageously be disposed between the cover plate 15 and the upper end surface 16 of the central portion.

The liquid reservoir 13 consists of an elongate, diagonally disposed recess in the central portion 5, being of the same orientation as the bone growth channel 9, 10, and with the two locking screws 7 and 8 located on either side of the reservoir. The reservoir extends in a vertical direction down through the central portion 5 so that only a thin partition 6a separates the bottom of the reservoir from the grooved recess 10. The capillary aperture 14 is centrally located in the bottom of the reservoir, while the inlet and outlet hoses have their connections further out towards the edges of the reservoir.

Figure 3:
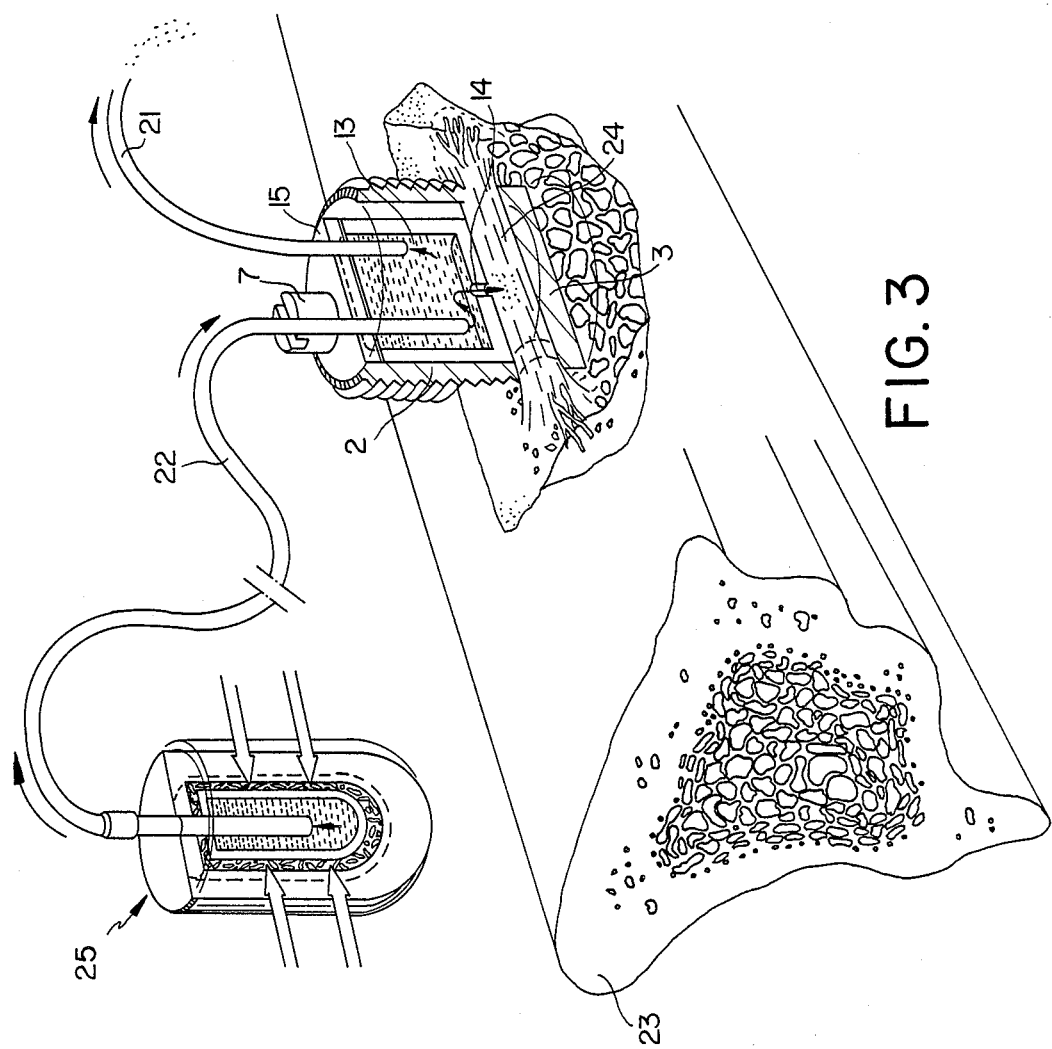
FIG. 3 schematically illustrates how the apparatus functions in the bone tissue of an animal.

In FIG. 3, the implant is shown surgically inserted in the tibia 23 in the one extremity of an experimental animal, for example a rabbit, such that the bone growth channel is located wholly beneath the defining surface of the bone. The figure shows partly how bone tissue 24 has grown into the channel and partly how the reservoir is filled with the test substance whose bone stimulating/retarding effect is to be examined. In this case, the chamber is connected, through an inlet hose 22, to a subcutaneous, osmotically acting minipump 25 of known type, for example ALZET model 2002, from ALZA Corp., California, USA. Hereby, the test substance may be continually administered for periods of weeks or more, such that a sufficiently high concentration will be maintained in the liquid volume. The outlet hose 21 is opened to subcutis and acts as a drainage.

A suitable size of implant may be: height 10 mm, diameter 6 mm. The openings 11, 12 of the bone ingrowth channel may be of a diameter of 1 mm. The diffusion capillary 14 is of a diameter of 0.25 mm and a length of 1 mm. The reservoir may have a volume of 10 microliters and the intake flow from the minipump 25 is, in this case, 0.5 microliters per hour. Hereby, there will be obtained a slow, continuous intake flow of liquid/test substance to the reservoir, which gives a concentration gradient along the diffusion capillary 14. The flow through the diffusion capillary will be low, since the reservoir is drained through the hose 21. The newly-formed bone tissue 24 which has grown into the channel is treated locally with the administered test substance without being disturbed by a flowing solution. Treated, or non-treated bone samples 26 (see FIG. 2) of approx. 5 mm in length and 1 mm in diameter may be removed at regular intervals from the implant and be examined.

The implant is inserted and functions as follows. An implant is inserted in each tibial metaphysis of an experimental animal by known atraumatic operational techniques. In this operation, it is ensured that the bone growth channel is localized in the cortical bone. After the operation, the implant is covered by the soft tissue, skin and fascia which is sutured. The one implant serves as a test implant, the test substance being administered during periods of weeks or more, while the other implant in the other extremity of the animal serves as a control reference implant. The test substance is supplied to the liquid reservoir of the test implant by means of an osmotically acting minipump of known type. There will hereby be obtained a slow, continuous inflow of the test substance, which ensures a sufficiently high concentration of the test substance in the liquid volume. The flow through the diffusion capillary will be negligibly low, since the reservoir is drained at the same time through the outlet conduit. After a bone formation period of approximately four weeks, the soft tissue is reopened, the locking screws are loosened and the central portion is removed. The newly-formed bone tissue in the form of cylindrical rods defined by the bone growth channels are stored in, for instance, formaldehyde prior to evaluation. The evaluation of the results is effected in that bone formation in the test implant inserted in the one extremity of the experimental animal is compared with the bone formation in the control implant in the other extremity. For purposes of quantification, use is made of databased microradiography which is known and does not form part of the present invention, see, for example, the reference "the Harvest Chamber . . . ", mentioned above.

The present invention should not be considered as restricted to the embodiment described above and shown on the drawings by way of example, but may be varied without departing from the spirit and scope of the appended claims. Hence, in certain cases, it may be sufficient that the test substance is supplied to the liquid reservoir through injection, or in the form of pellets with a slow release of the test substance.

What we claim and desire to secure by letters patent is:

1. An apparatus of a bio-compatible material for implantation in a living bone tissue and for studying bone tissue formation growth in an implant in response to a locally administered test substance, said apparatus comprising;
   an outer portion with a central recess extending therethrough and a removable inner portion insertable in said central recess;
   means provided in at least a bottom wall of said outer portion cooperating with a bottom wall of said inner portion to form a bone tissue ingrowth channel when said inner portion is fully inserted into said central recess, said channel being exposable for access thereto when said inner portion is removed upwardly, thereby allowing examination of said bone tissue ingrowth in said channel; and
   a reservoir provided in said inner portion, said reservoir including means for fluid communication with said bone tissue ingrowth channel for supplying said test substance to said bone tissue ingrowth channel.

2. An apparatus according to claim 1, wherein said means forming said bone tissue ingrowth channel includes a first groove formed in the bottom wall of said outer portion and a second groove corresponding to said first groove and aligned therewith to form said channel when said inner portion is fully inserted into said central recess.

3. The apparatus as claimed in claim 1, wherein said inner and outer portions are made of pure titanium.

4. The apparatus as claimed in claim 1, wherein said inner and outer portions have at least those surfaces which come into direct contact with the bone tissue, coated with pure titanium.

5. The apparatus as claimed in claim 2, wherein said inner and outer portions have at least those surfaces which come into direct contact with the bone tissue, coated with pure titanium.

6. The apparatus as claimed in claim 1, wherein said reservoir includes a cavity provided in said inner portion and extending therethrough to communicate with said bone tissue ingrowth channel and wherein said means for fluid communication includes a capillary aperture for the supply of the test substance without simultaneous liquid flow.

7. The apparatus as claimed in claim 2, wherein said reservoir includes a cavity provided in said inner portion and extending therethrough to communicate with said bone tissue ingrowth channel and wherein said means for fluid communication includes a capillary aperture for the supply of the test substance without simultaneous liquid flow.

8. The apparatus as claimed in claim 6, wherein said reservoir includes an elongate, diagonally disposed cavity of substantially the same orientation as said bone tissue ingrowth channel and two holes extending through said outer and inner portions for receiving locking screws for fixed interlocking of said inner and outer portions.

9. The apparatus as claimed in claim 8, wherein said two holes extend through said inner portion on opposite sides of said elongate cavity.

10. The apparatus as claimed in claim 9, wherein said reservoir is upwardly covered by a cover plate which is locked to the upper end surface of said inner portion by locking screws received in said holes.

11. The apparatus as claimed in claim 10, wherein said cover plate is provided with two openings at the location above said liquid reservoir for receiving hoses for supply and removal (drainage), respectively, of the test substance.

12. The apparatus as claimed in claim 11, wherein said reservoir is connected to a subcutaneous, osmotically acting minipump for continuous supply of the test substance to said bone tissue ingrowth channel during a predetermined period of time.

* * * * *